United States Patent
Baker

[19]
[11] Patent Number: 6,132,429
[45] Date of Patent: Oct. 17, 2000

[54] RADIOFREQUENCY MEDICAL INSTRUMENT AND METHODS FOR LUMINAL WELDING

[76] Inventor: James A. Baker, 4292-P Wilkie Way, Palo Alto, Calif. 94306

[21] Appl. No.: 09/251,962

[22] Filed: Feb. 17, 1999

Related U.S. Application Data

[60] Provisional application No. 60/074,808, Feb. 17, 1998.

[51] Int. Cl.[7] .................................................. A61B 18/14
[52] U.S. Cl. .................................. 606/50; 606/38; 606/40
[58] Field of Search ........................... 606/45, 46, 48–52, 606/38, 40

[56] References Cited

U.S. PATENT DOCUMENTS

| | | | |
|---|---|---|---|
| 5,151,102 | 9/1992 | Kamiyama et al. | 606/51 |
| 5,269,780 | 12/1993 | Roos | 606/51 |
| 5,290,287 | 3/1994 | Boebel et al. | 606/51 |
| 5,403,312 | 4/1995 | Yates et al. | 606/50 |
| 5,443,463 | 8/1995 | Stern et al. | 606/51 |
| 5,693,051 | 12/1997 | Schulze et al. | 606/51 |
| 5,702,390 | 12/1997 | Austin et al. | 606/48 |
| 5,833,690 | 11/1998 | Yates et al. | 606/51 |
| 5,891,141 | 4/1999 | Rydell | 606/51 |
| 6,039,733 | 3/2000 | Buysse et al. | 606/40 |

*Primary Examiner*—Lee Cohen
*Attorney, Agent, or Firm*—Fish & Neave; Nicola A. Pisano

[57] ABSTRACT

Methods and apparatus are provided for welding or sealing vessels or organs by collapsing and elongating a vessel with a jaw-like structure, and then applying an RF current between first and second bi-polar electrodes to weld the approximated vessel walls together. The jaw-structure is configured to progressively collapse the section of tissue to squeeze fluids out of the lumen of the vessel. The device also may include one or more sensors providing signals to a power controller that modulates application of RF energy to the vessel based on power, temperature or tissue impedance.

20 Claims, 12 Drawing Sheets

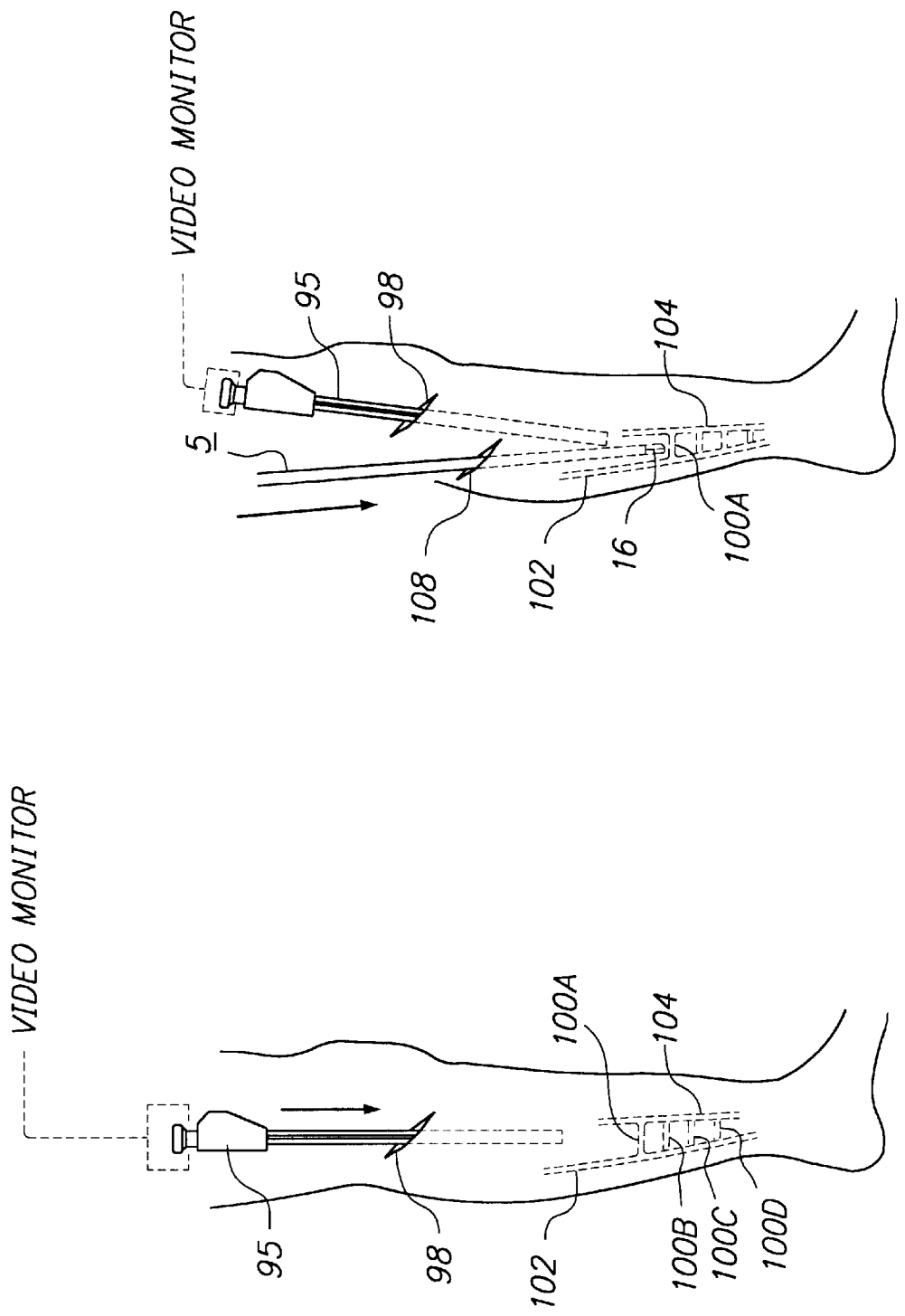

RADIOFREQUENCY MEDICAL INSTRUMENT AND METHODS FOR LUMINAL WELDING

REFERENCE TO RELATED APPLICATIONS

This application claims priority from U.S. provisional patent application Serial No. 60/074,808, filed Feb. 17, 1998. This application also is related to co-pending U.S. patent application Ser. No. 08/920,291, filed Aug. 28, 1997, now U.S. Pat. No. 5,957,920, and Ser. No. 09/191,413, filed Nov. 12, 1998, which are hereby incorporated herein by reference.

FIELD OF THE INVENTION

This invention relates to methods and apparatus for utilizing RF energy to seal tubular vessels of organs, and more particularly for delivering RF energy in a controlled manner to denature proteins in luminal tissues to weld closed the lumen, for example, in a blood vessel of any size.

BACKGROUND OF THE INVENTION

In both open and endoscopic surgeries, it often is necessary to seal or weld blood vessels, both veins and arteries, ranging in size from less than 1 mm in diameter to more than 6 mm in diameter. For example, in subfacial endoscopic perforator surgery or SEPS, a series of perforator vessels in a patient's leg are sealed closed to alleviate venous ulcerations. In a typical SEPS procedure, the surgeon uses a mechanically deformable clip to pinch off such perforator vessels. A single clip may not seal a vessel in a reliable manner and the surgeon typically uses multiple clips on each perforator vessel to assure an effective seal. It would be preferable to seal a vessel without leaving a metal clip implanted in the patient's body.

Radiofrequency ("RF") instruments for sealing blood vessels have been developed. An example of a previously known bi-polar grasper, shown in FIG. 1A, typically applies from 40 watts to 100 watts or more of power to the exterior of a vessel to cauterize such vessels or vascularized tissue masses. To use such previously known bi-polar instruments, a blood vessel is squeezed between the opposing jaw faces of the grasper (see FIG. 1B). Each jaw face carries a conductive electrode 2A, 2B. When operating in a bi-polar fashion, an RF current generally flows directly between electrodes 2A and 2B, and "across" vessel 3, as indicated by the arrow in FIG. 1B.

Additionally, there may be stray RF current flow in circuitous low resistance routes, e.g., outwardly along the vessel and then through surrounding tissue, to reach the other electrode. This type of stray RF current flow is undesirable. For example, in a SEPS procedure or when sealing a branch vein of any arterial conduit that may be mobilized for a bypass, it is undesirable to have stray RF current affect the arterial conduit.

In using a previously known device such as depicted in FIGS. 1A–1B, the impedance of the tissue of the vessel wall changes continuously during the application of RF, making sealing erratic. The high levels of power typically used in previously known devices (e.g., 40 to 100 watts), makes the tissue impedance levels undesirably change very rapidly. At power levels ranging from 40 to 100 watts, impedance levels typically will increase within a few seconds to a level such that RF energy flow is impeded or restricted altogether, and may contribute to an increase in stray RF current. Moreover, the vessel walls often will not be fused together over a sufficient area to provide an effective seal.

Furthermore, previously known devices, such as shown in FIGS. 1A–1B, which simply clamp the vessel walls together, often entrap blood between the luminal surfaces. This trapped blood acts as a heat sink and may adversely affect the uniformity of RF thermal effects. It has been observed that the entrapment of blood within the lumen significantly interferes with the binding characteristics of the denatured proteins that are created and that comprise the amalgam for fusing the vessel walls together.

It would therefor be desirable to provide an RF energy delivery system, and methods of use, that control the effects of variable tissue impedance, thereby allowing an effective energy delivery profile in the tissue targeted for welding.

It also would be desirable to provide an RF energy delivery system, and methods of use, wherein an openable/closeable working end reduces the risk of entrapping blood between the vessel walls.

It further would be desirable to provide an RF energy delivery system, and methods of use, that reduce tissue charring and smoke, which can obscure the physician's view, particularly in endoscopic surgeries.

It still further would be desirable to provide an RF energy delivery system, and methods of use, that reduce the outward spread of thermal effects along a vessel.

SUMMARY OF THE INVENTION

In view of the foregoing, it is an object of this invention to provide an RF energy delivery system, and methods of use, that reduce the unwanted effects of variable tissue impedance, thereby allowing an effective energy delivery profile in the tissue targeted for welding.

It is also an object of this invention to provide an RF energy delivery system, and methods of use, wherein an openable/closeable jaw structure reduces the risk of entrapping blood between the vessel walls.

It is a further object of the present invention to provide an RF energy delivery system, and methods of use, that reduce tissue charring and smoke, which can obscure the physician's view, particularly in endoscopic surgeries.

It is another object of this invention to provide an RF energy delivery system, and methods of use, that reduce the outward spread of thermal effects along a vessel (e.g., to protect a main vessel when sealing branch vessels close to main vessel).

These and other objects of the present invention are accomplished by providing apparatus and methods for applying RF energy to tissue that: (1) progressively engage a vessel or organ to minimize the amount of blood entrapped in the lumen, and thereafter maintain the vessel walls in close approximation under appropriate pressures for welding; (2) deliver bi-polar RF energy longitudinally along the length of the vessel to create an effective seal; (3) stretch the targeted vessel segment prior to application of the RF energy to alter its impedance characteristics; and optionally (4) control RF energy delivery during treatment by means of feedback from sensors proximate to the targeted tissue.

A preferred embodiment of an instrument of the present invention comprises an introducer member that carries a distal working end with an openable/closeable jaw structure for engaging a targeted vessel section. The jaw structure is moveable between an open position and a closed position by a suitable mechanism disposed in a handle portion coupled to the introducer member. The jaw structure has a proximal jaw side or member and a distal jaw side or member with cooperating opposing jaw faces.

Each jaw face defines left-side and right-side portions that cooperate with the opposing jaw member. The distal jaw side includes a central projecting portion. The proximal jaw face has deflectable left-side and right-side portions with a central receiving structure or gap for receiving the opposing side's projecting portion. The cooperating jaw faces (projecting and receiving portions) serve several purposes.

First, the deflectable left-side and right-side portions of the proximal jaw face deflect outward when the jaws close to progressively engage the vessel from the center of the targeted vessel section and cause blood within the lumen to be squeezed out of the treatment area. Second, the deflectable receiving jaw faces may be designed to stretch the vessel before RF delivery to alter the impedance characteristics of the targeted vessel section. Also, the deflectability of the left-side and right-side portions of the jaw face in the closed position allows the jaw structure to accommodate vessels of different diameters and maintain the luminal surfaces (when collapsed) within a particular pressure range that is suitable for an RF-induced thermal biological weld.

First and second bi-polar electrodes disposed on the left-side and right-side portions of the jaw assembly provide a flow of current longitudinally through the targeted vessel section that has been engaged and extended. Optionally, the jaw assembly also carries one or more sensors for measuring temperatures and/or impedance levels of the section of the vessel targeted for welding, contemporaneous with RF energy delivery. A power controller and feedback circuitry also may be provided to regulate RF energy delivery to the targeted vessel section responsive to measured tissue temperatures or tissue impedance, or both.

A preferred method of the present invention for welding closed the lumen of a blood vessel (or vessels within vascularized tissue) comprises: (1) targeting a longitudinal length of a blood vessel for welding that defines left and right end sections; (2) progressively engaging the targeted vessel section by first engaging a center section and squeezing substantially all of the blood from the vessel lumen; and (3) optionally, stretching the longitudinal length of the targeted vessel section engaged with the working end; (4) delivering RF energy from the left end to the right end (or vice versa) of the vessel section in a longitudinal manner with bi-polar current flow from a first electrode at one end of the vessel section to a second electrode at the other end of the vessel section.

The methods of the present invention may, in additional, include steps of providing temperature and impedance measuring circuitry, feedback circuitry, and a power controller, and using those components to regulate the delivery of RF energy to a targeted vessel section.

BRIEF DESCRIPTION OF DRAWING

Additional objects and advantages of the invention will be apparent from the following description, the accompanying drawings and the appended claims, in which:

FIGS. 6 and 7 are schematic views of a SEPS procedure performed using the instrument and methods of the present invention;

DETAILED DESCRIPTION OF THE INVENTION

Figure 1A:
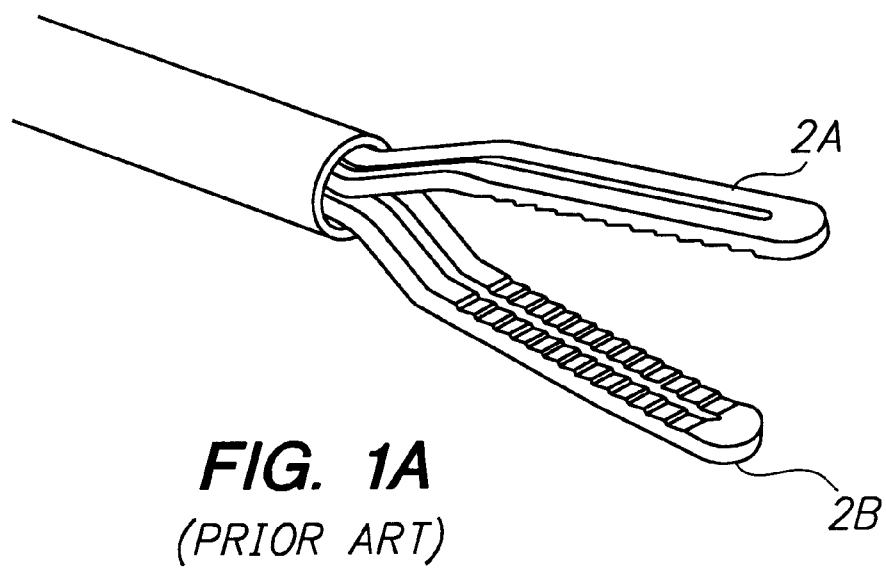
FIGS. 1A–1B are perspective views of a jaw structure of a previously known radiofrequency device and its use in cautery.

The present invention provides apparatus and methods for controlling the effects of RF energy delivery to a blood vessel captured within a working end of an instrument to improve RF energy delivery profiles for welding small and large blood vessels (or other organs) quickly and efficiently.

The apparatus and methods of the present invention may be used to seal or weld blood vessels in a number of different procedures. For purposes of illustration, the present invention is described for use in performing subfacial endoscopic perforator surgery (SEPS). In this disclosure, the term vessel is defined to include any artery or vein of any size, and further includes tissue/vessel combinations or vascularized tissue masses where an individual vessel cannot be separated from the tissue. The apparatus and methods of the present invention also find application in sealing the lumens of other organs or anatomic structures having lumens with collagen-containing tissues capable of forming biological glue.

The mechanism of tissue welding is complex and is not well understood. The application of RF energy to tissue results in heat which denatures tissue proteins in the vessel walls and in the endothelial lining of the vessel, which includes a type of collagen. The heat denatures such proteins, including collagen, into a proteinaceous amalgam, which forms a thermal biological glue in a temperature range from 65° C. to 90° C. The integrity of the sealing effect depends greatly on the conductive characteristics of the target tissue.

To form an effective seal, it is necessary to maintain a desired temperature over the targeted vessel section for an appropriate time period to develop a uniform layer of denatured proteins. Even partial denaturation of the endothelial lining involves disruption of cellular membranes, thereby allowing cellular fluids and extracellular matrix materials to intermix. The resultant thermally elevated amalgam of denatured proteins bind together to create a biological weld. When the source of thermal energy is removed, the proteins re-nature and fuse the luminal walls together. As the vessel heals over time, the biological weld is reabsorbed by the body via the wound healing process.

Several variables come into play when using RF energy to elevate luminal tissues to the levels required to denature proteins. For purposes of the present invention, the energy source may be a previously known RF generator operating with a high frequency alternating current (e.g., from 55,000 Hz to 550,000 Hz) that is adapted to flow from (or between) one or more electrodes through the vessel walls targeted for welding. As is known, the application of such alternating current causes ionic agitation and friction in the targeted tissue as ions (generally within extracellular matrices and not within intracellular fluids) follow the changes in direction of the alternating current. Such ionic agitation or frictional heating does not result from direct tissue contact with a resistive electrode.

In the delivery of energy to a tissue mass, I=E/R, where I is the intensity of the current in amperes, E is the energy potential measured in volts and R is the tissue resistance measured in ohms. Current density, or the level of current intensity, is an important gauge of energy delivery, and relates to the impedance of the targeted tissue mass. The level of heat generated within the target tissue thus is influenced by several factors, such as (i) RF current intensity, (ii) RF current frequency, (iii) impedance levels within the targeted tissue disposed between the electrodes, which vary during a treatment cycle, (iv) heat dissipation from the targeted tissue; (v) duration of RF energy delivery, and (vi) distance traveled through the targeted tissue by the RF current between the conductive electrodes.

Figure 2:
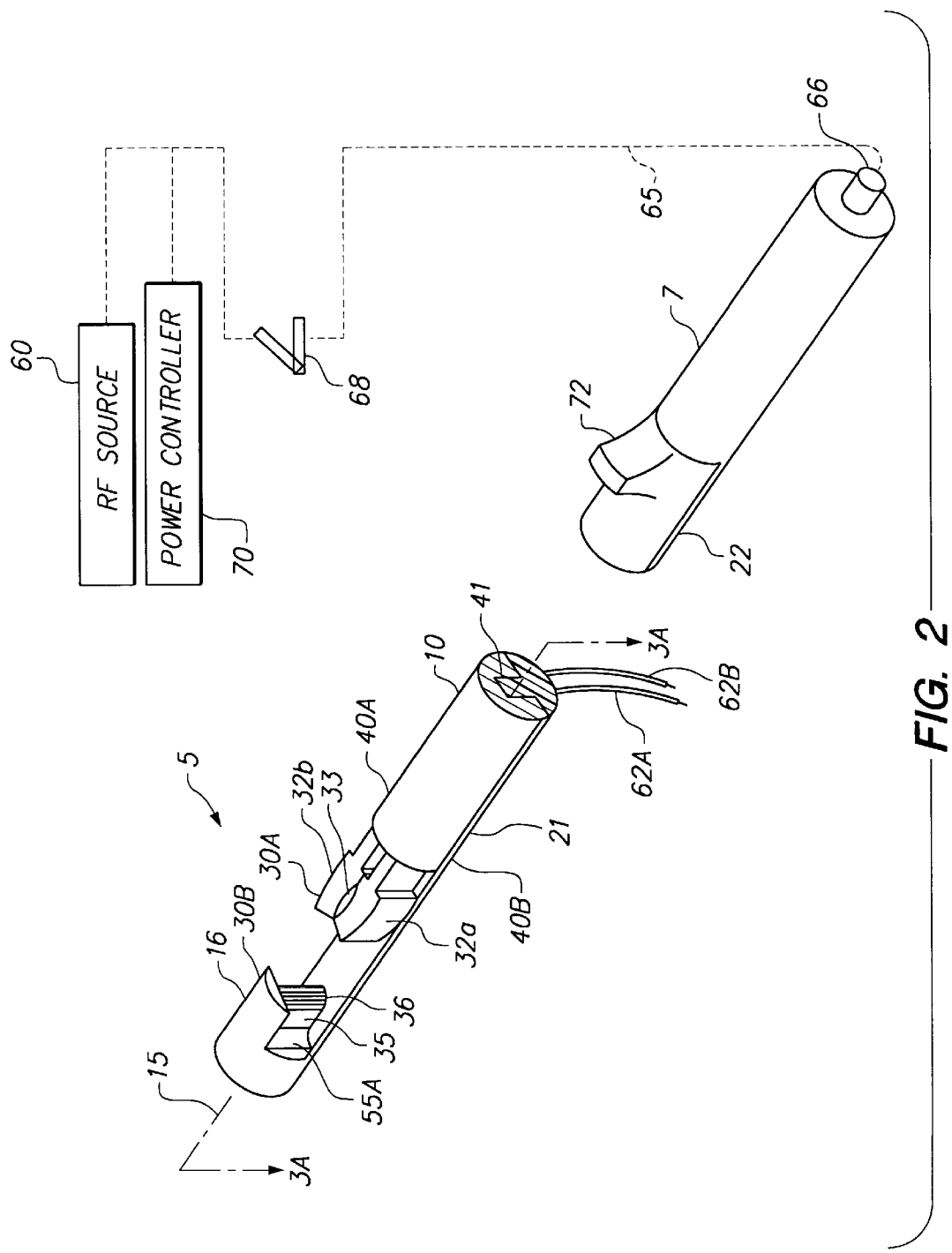
FIG. 2 is a perspective view of a first embodiment of an instrument of the present invention.

Referring now to FIG. 2, a preferred embodiment of instrument 5 constructed in accordance with the present invention is described. Instrument 5, which is adapted for open or endoscopic procedures with handle portion 7, is coupled to elongate introducer portion 10 extending along axis 15 and carrying distal working end 16. Introducer portion 10 with proximal and distal ends, 21 and 22, respectively, illustratively has a cylindrical cross-section and is made of suitable biocompatible materials, such as metal or plastic. Introducer portion 10 preferably has an outer diameter ranging from 5 mm to 10 mm, e.g., to cooperate with a standard endoscopic trocar sleeve.

Figure 3A:
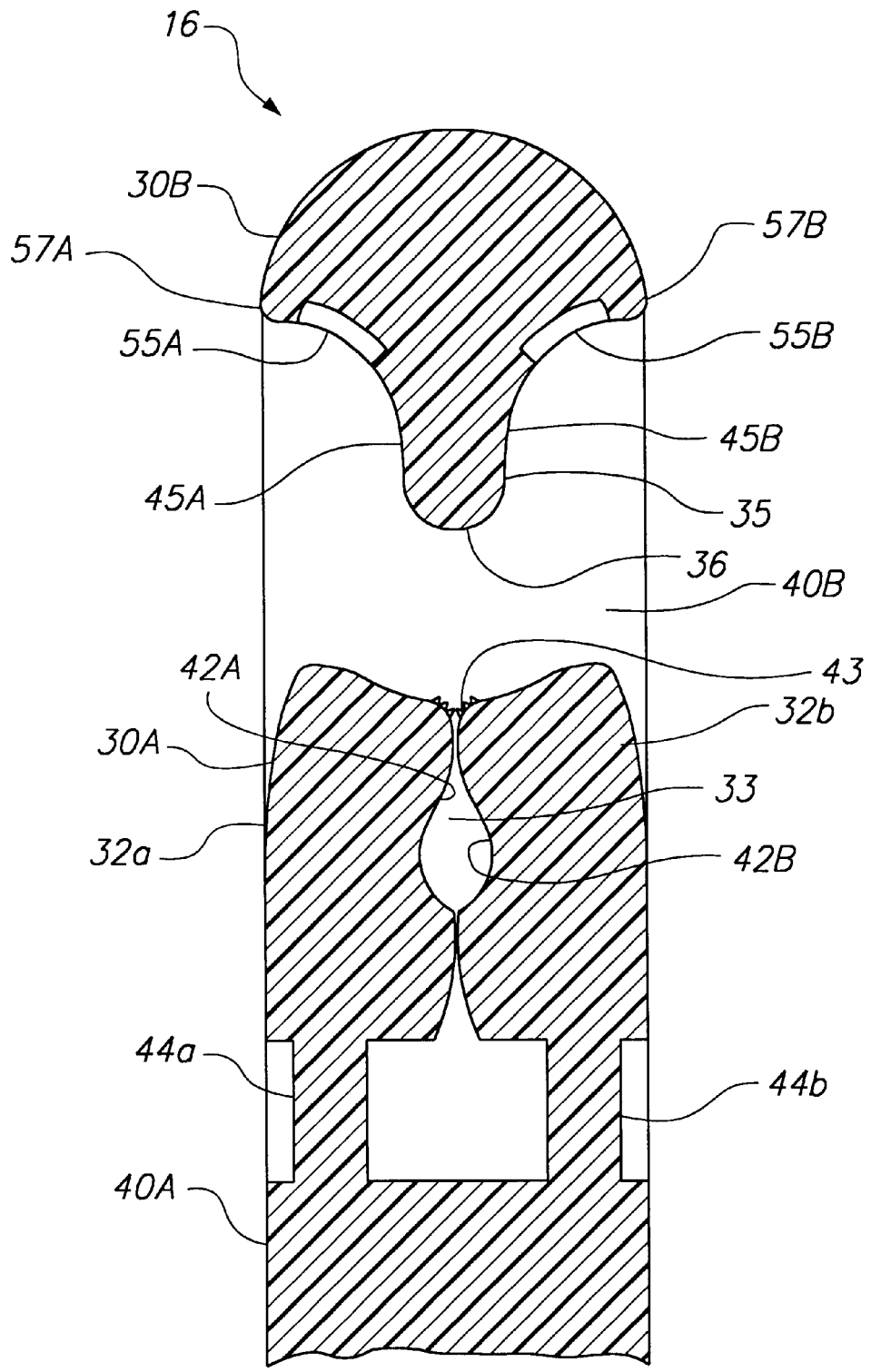
FIGS. 3A–3B are, respectively, enlarged sectional views of the working end of the device of FIG. 2 with the jaw assembly and jaw sides in the open and closed positions.
Figure 3B:
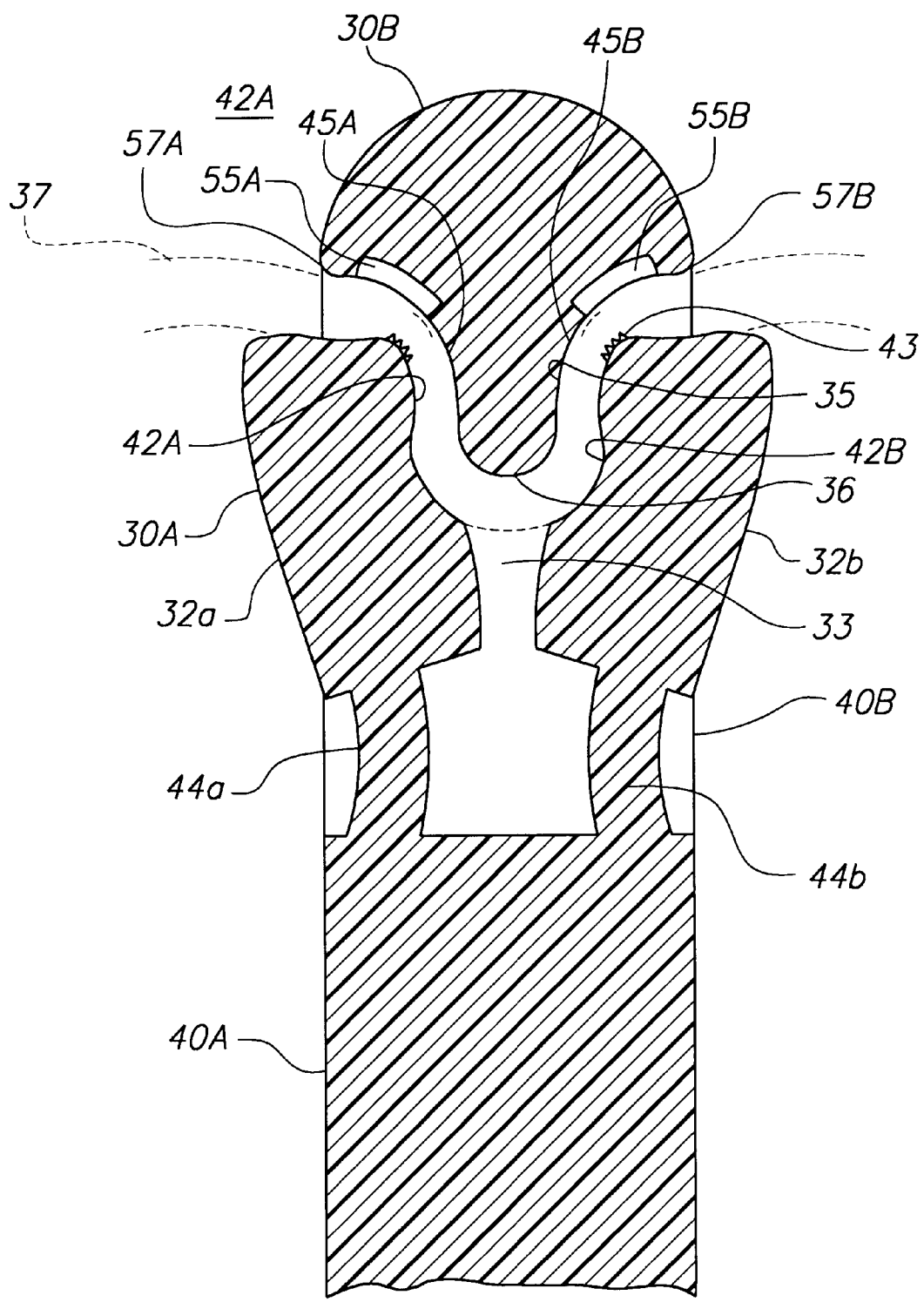
Figure 4A:
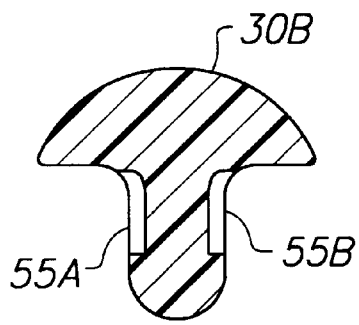
FIGS. 4A–4D depict alternative cross-sectional shapes of a distal jaw side of the assembly of the present invention.
Figure 4B:
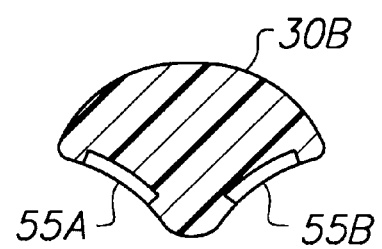
Figure 4C:
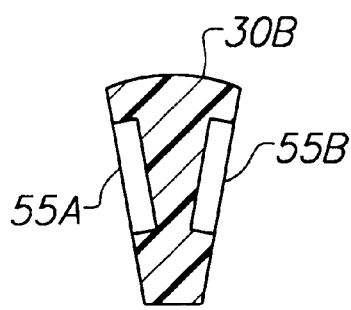
Figure 4D:
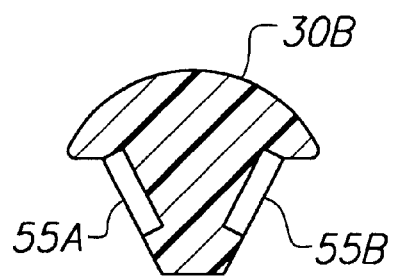

Referring now also to FIGS. 3A–3B, working end 16 comprises an openable/closeable jaw assembly with first and second sides or faces 30A and 30B carried by introducer portion 10. Proximal jaw face 30A is configured as a resilient structure with left and right arms 32a and 32b defining space or gap 33 therebetween. Arms 32a and 32b are adapted to at least partly straddle centered projecting portion 35 of distal jaw face 30B when closing. Proximal jaw side 30A is moveable relative to distal jaw side 30B from an open position (shown in FIGS. 2 and 3A) and various converging positions (not shown) towards the closed position of FIG. 3B (tissue 37 is shown by phantom lines).

Introducer portion 10 has a first extension member 40A that carries proximal jaw side 30A of working end 16. First extension member 40A slidably cooperates with second extension member 40B that carries distal jaw side 30B of the working end. The first and second extension members 40A and 40B may cooperate by any suitable means known in the art such (such as inner and outer tubular concentric members) and are illustratively depicted as interlocking keyed members with keyed spline 41 (key not shown) as may be made of a plastic injection-molded material. Proximal and distal jaw sides 30A and 30B of working end 16 are of a medical grade plastic or other nonconductive material or are otherwise insulated from the RF electrodes carried within the jaw assembly, which are described in greater detail below.

Proximal jaw side 30A comprises left-side jaw face portion 42A and right-side jaw face portion 42B on arms 32a and 32b, respectively, which arms are capable of deflecting or flexing away from center projecting portion 35 of distal jaw face 30A. Each left-side and right-side jaw face 42A and 42B optionally may have a grip texture 43 (including serrations, hatching, projecting points, etc.) covering its vessel-engaging surface for gripping a vessel. As may be observed by comparing FIG. 3A and FIG. 3B, arms 32a and 32b flex or pivot about flex portion 44a and 44b of the arms. Alternatively, each arm may be pivotable about a pin (not shown) with a spring urging the arm inward toward axis 15.

In operation, when left-side and right-side jaw faces 42A and 42B close toward the proximal-most edge 36 of cooperating projecting portion 35, and upon contacting edge 36, arms 32a and 32b deflect outward. This movement of arms 32a and 32b in turn causes faces 42A and 42B to slide along left-side face 45A and right-side face 45B, respectively, of projecting portion 35. FIG. 3B shows tissue 37 in phantom view engaged by working end 16. The axial force required to be applied on extension member 40A to cause arms 32a and 32b to deflect around projecting portion 35 is not high, and is determined by the spring constant of the resilient material of flex portions 44a and 44b.

That resilient material preferably is selected to provide sufficient resistance to outward deflection of arms 32a and 32b to collapse a blood vessel and then to maintain a length of the captured vessel under pressure, thereby insuring the walls of the vessel lumen are in suitable contact for welding. Thus, cooperation of left-side and right-side faces 42A and 42B when sliding around left-side and right-side faces 45A and 45B of projecting portion 35 progressively engages the vessel, from its center outward, to squeeze blood from the lumen. Moreover, cooperation of left-side and right-side faces 42A and 42B when sliding around left and right-side faces 45A and 45B stretches the vessel section around projecting portion 35. The extent of such stretching or vessel elongation is partly dependent on grip texture 43 impressed on left-side and right-side faces 42A and 42B and the resistance to flexing engineered into arms 32a and 32b.

Referring still to FIGS. 3A and 3B, the cross sectional shape of projecting portion 35 has an arcuate shape with right-side and left-side face portions 45A and 45B that extend into gap 33 between arms 32a and 32b and the cooperating curved surfaces thereof. Cooperating faces 42A and 42B and 45A and 45B, respectively, may be have any suitable planar or curved cross-section relative to one another, and still squeeze the blood from the lumen as a blood vessel is collapsed. FIGS. 4A–4D depict alternative cross-sectional shapes of distal jaw side 30B of an openable/closeable jaws structure having projecting portion 35. The cooperating proximal jaw side 30A (not shown) for the distal jaw 30B depicted in FIGS. 4A–4D would include a curved or linear mating surface for surfaces 45A and 45B.

In FIGS. 3A–3B, left-side and right-side faces 45A and 45B, respectively, of projecting portion 35 carry cooperating left-side and right-side electrodes 55A and 55B and are adapted to operate in a bi-polar manner. The electrodes are positioned in the faces 45A and 45B so as to provide laterally-outward insulated portions 57A and 57B that insure that the electrodes are not exposed on an outermost surface of the working end 16 in the jaw-closed position. This prevents hot electrodes from contacting tissue surfaces other than the targeted vessel. Electrodes 55A and 55B comprise a suitable electrically conductive material, such as gold, nickel titanium, platinum, stainless steel, aluminum or copper.

Referring again to FIG. 2, RF source or generator 60 is provided for delivering RF current to the electrodes that contact the vessel within the jaw assembly. Thus, the electrode pair is adapted to send RF current between left-side electrode 55A and right-side electrode 55B through the targeted longitudinal section of vessel captured in working end 16. It should be appreciated that the left-side and right-side electrodes 55A and 55B may be disposed on either the proximal or distal parts of working end 16, so long as they contact the engaged blood vessel to deliver RF current longitudinally through the vessel section. In the embodiment of FIGS. 2 and 3, electrodes 55A and 55B are disposed on distal jaw side 30B, but alternatively may be disposed in left-side and right-side faces 42A and 42B of arms 32a and 32b.

With reference still to FIG. 2, individual current-carrying wires 62A and 62B carry bi-polar RF energy to and from paired conductive electrodes 55A and 55B. Wires 62A and 62B extend through handle portion 7 to power transmission cable 65, which is connected via detachable coupling 66 to an energy source, such as a previously known RF generator or source 60. Bi-polar RF current may be switched on and off by foot pedal 68, or any other suitable means such as a switch in handle 7 (not shown). Optional power controller 70, described in more detail hereinbelow, is coupled to instrument 5 and RF source 60 via cable 65.

Thumb grip 72 formed in extension member 40A is movable back and forth as a jaw-actuating mechanism to move proximal jaw side 30A relative to distal jaw side 30B between an open position (FIG. 3A), wherein the proximal side 30A and distal side 30B are moved apart for receiving a vessel segment, and a closed position (FIG. 3B), wherein the proximal and distal sides 30A and 30B converge together for engaging a vessel segment. Extension member 40A that carries proximal side 30A may be biased to the open position by spring (not shown). As will of course be understood, other mechanisms known in the art may be employed for actuating the proximal and distal sides 30A and 30B between the open and closed positions, for example, a pistol grip handle with a trigger or lever arm may be used.

Figure 5:
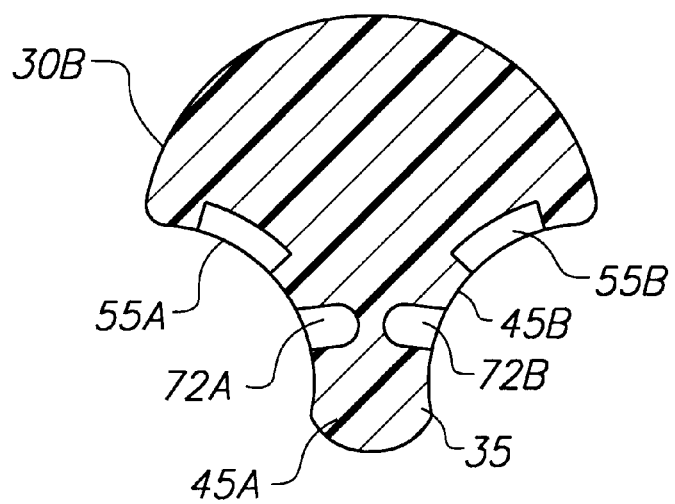
FIG. 5 is a sectional view of an alternative working end of the device of FIG. 2 including thermal sensors.

With respect to FIG. 5, an alternative embodiment is described that includes an array of individual sensors 72A and 72B carried in a portion of the jaw assembly that contacts the blood vessel section being welded. Sensors 72A–72B preferably are located slightly spaced apart from electrodes 55A and 55B, and measure temperatures of tissue adjacent to the active electrodes during a vessel welding operation. Alternatively, sensors 72A and 72B may be replaced by more or fewer sensors, and may be configured to measure the temperatures of the electrodes, rather than the adjacent tissue. Each sensor of an array preferably comprises a thermocouple, e.g., a T-type thermocouple formed from paired dissimilar metals such as copper and constantan, or a thermistor (i.e., a temperature sensor that has a resistance that varies with the temperature level).

Referring now to FIGS. 6 and 7, operation and use of the instrument of FIG. 2 in performing a method of the invention is described. First, the surgeon inserts endoscope 95 (or any other suitable instrument) into a patient's leg through first incision 98, to dissect an access path to perforator 100A between superficial vein 102 and deep vein 104. It should be appreciated that there may be from one to ten or more perforator vessels that must be sealed in a SEPS procedure; four perforators 100A–100D are shown in FIG. 6. FIG. 7 next shows the surgeon introducing the distal end of instrument 5 through second incision 108 and advancing it towards the location of perforator 100A. The access space around the perforators may be dissected and retracted mechanically or by insufflation by known means (not shown).

Figure 8A:
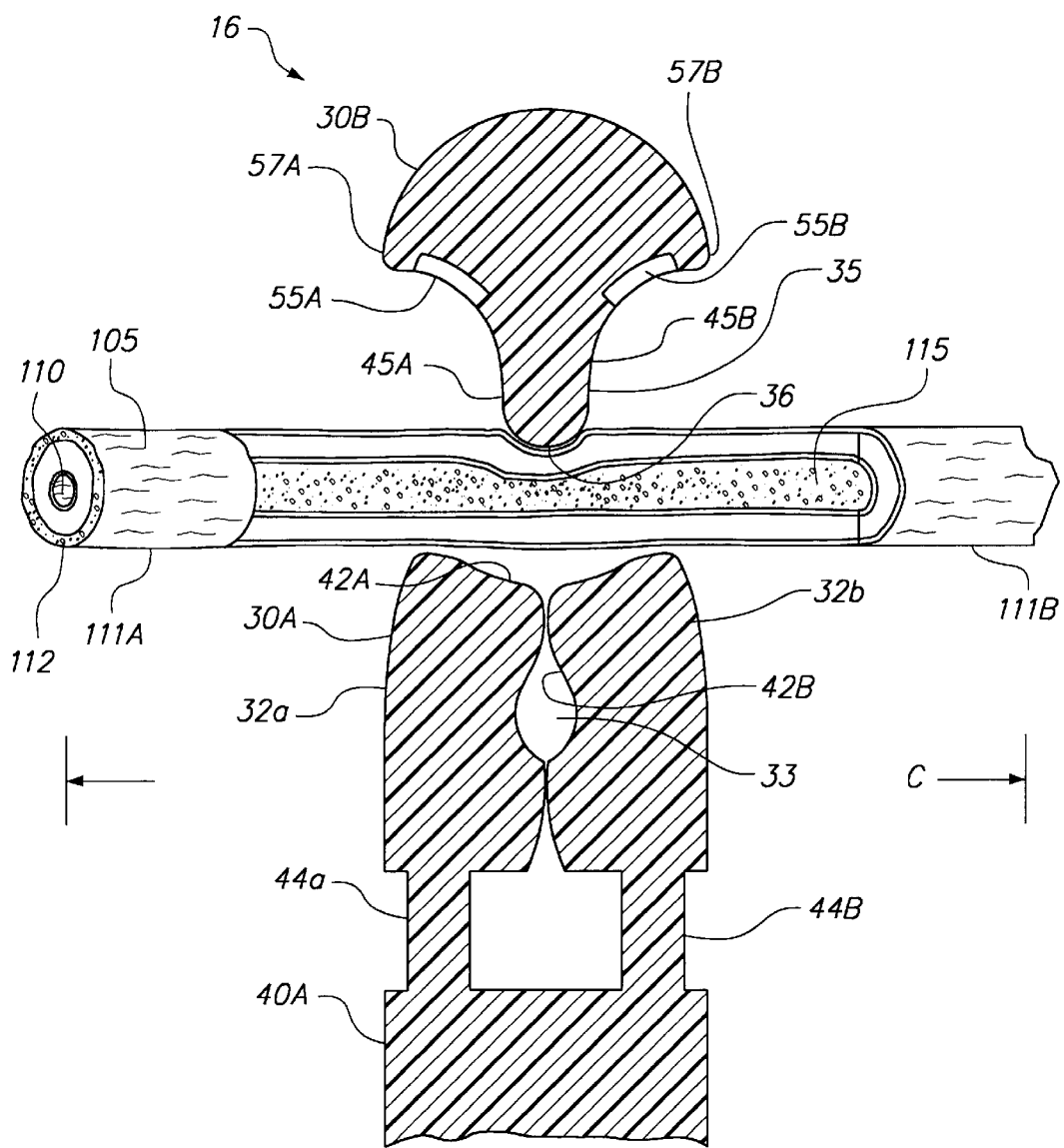
FIGS. 8A–8D are sectional views of a portion of a blood vessel targeted for treatment depicting, in sequence, a method of the present invention to weld or seal the blood vessel lumen.

FIG. 8A is an enlarged view representing a particular longitudinal section 105 of perforator 100A (or any other blood vessel) that is targeted for sealing in the interior of the patient's body. The surgeon generally identifies a vessel section 105 which is bounded by left and right ends portions 111A and 111B and is positioned between jaw sides 30A and 30B in the open position. The vessel has lumen 110 and endothelium 112 with blood 115 within. Left and right ends 111A and 111B are spaced apart a distance C, as described further below.

Figure 8B:
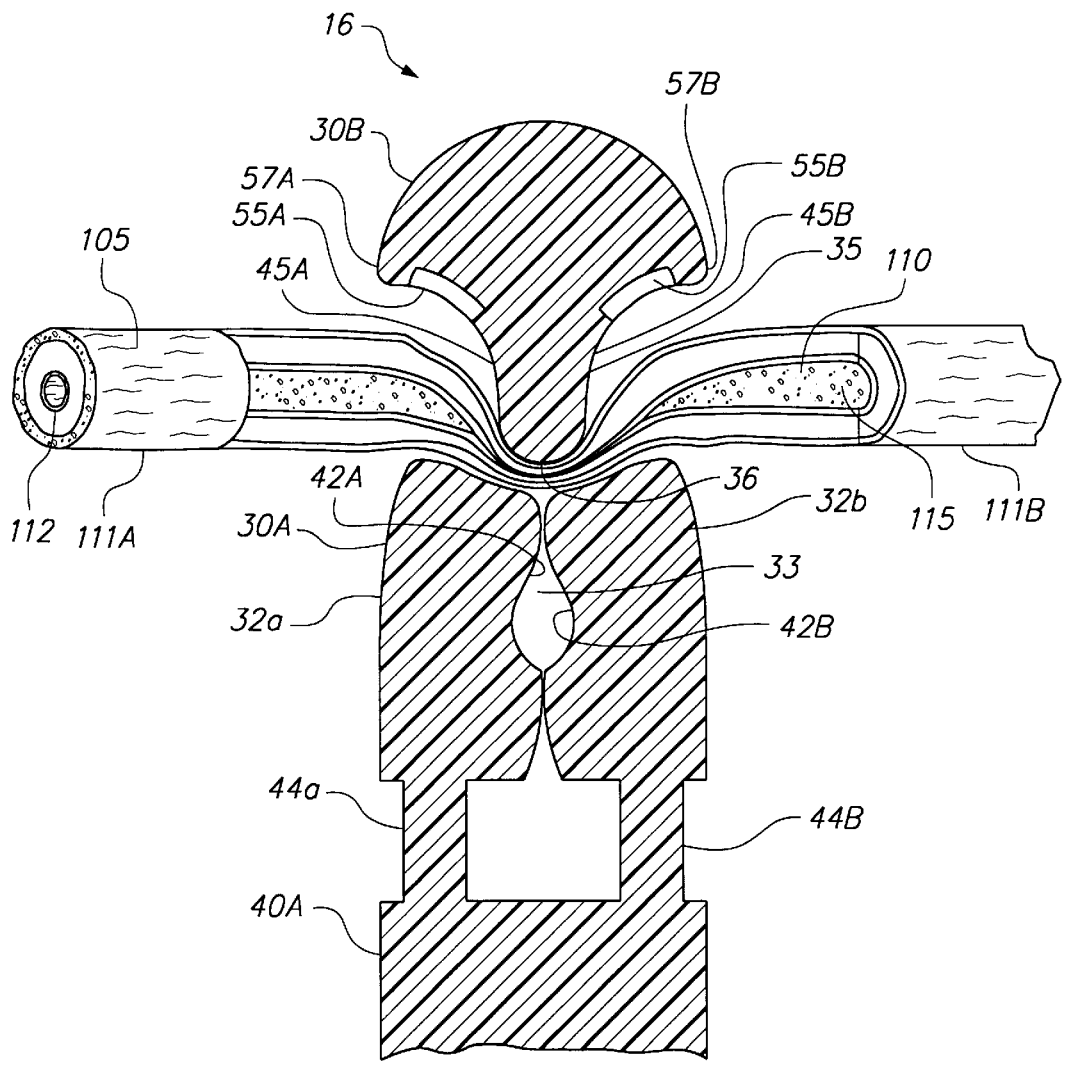

With respect to FIG. 8B, the surgeon progressively moves the jaws toward the closed position, so that left-side and right-side faces 42A and 42B of proximal jaw side 30A press and collapse the vessel against proximal-most edge 36 of projecting portion 35. Thus, as lumen 110 is collapsed at a center portion of the targeted vessel section, flow of blood 115 through the vessel is pinched off and terminated.

Figure 8C:
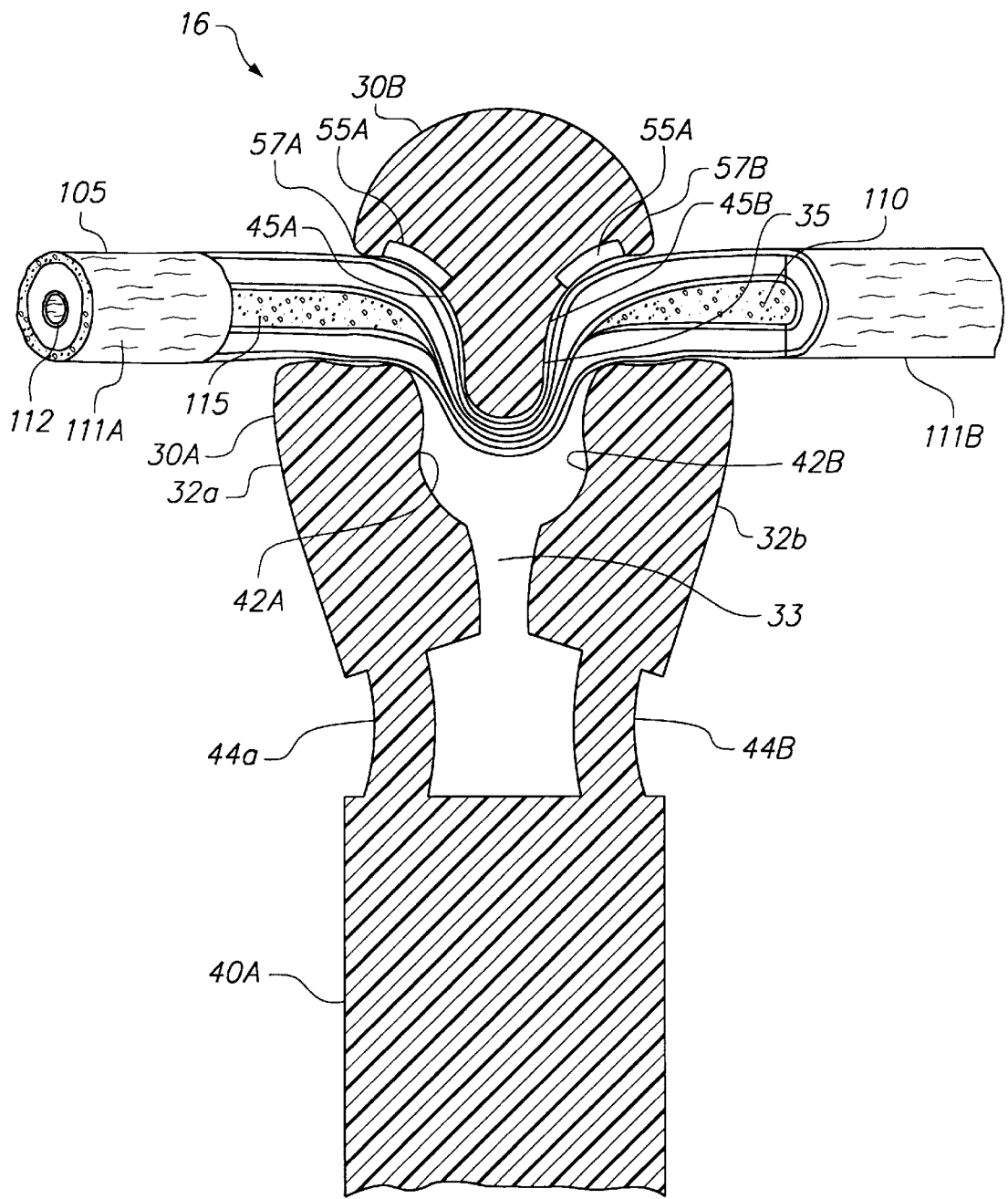
Figure 8D:
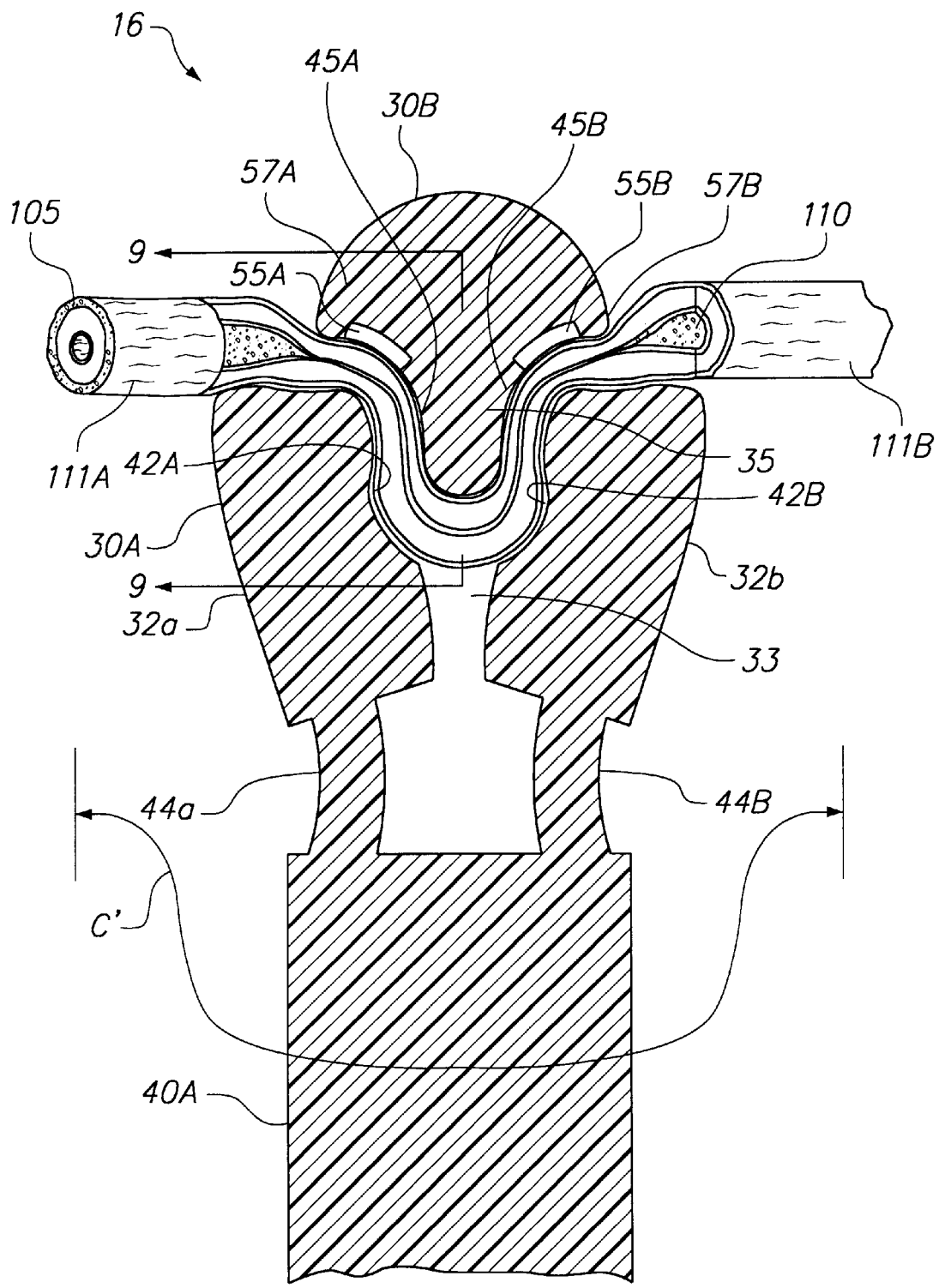

Referring next to FIGS. 8B and 8C, as vessel progressively collapses further, substantially all of the blood is squeezed from the vessel segment targeted for sealing. In particular, left-side and right-side jaw faces 42A and 42B carried by deflectable arms 32a and 32b slidably move over the vessel relative to faces 45A and 45B of opposing jaw side 30B. In contrast to previously known jaw arrangements, which may trap blood between approximated vessel walls, the progressive sliding movement of portions of jaw faces 42A and 42B relative to the opposing jaw faces 45A and 45B causes substantially all blood 115 to be pushed out of the targeted vessel section. FIG. 8D shows the vessel section 105 captured in the working end 16 in the closed position, ready for RF energy delivery.

FIGS. 8A–8D also depict another aspect of the methods of the invention is described, in which the targeted vessel section is stretched or elongated as it is engaged by working end 16. In particular, targeted vessel section 105 is stretched lengthwise when left end 111A and right end 111B move apart, relative to the axis of the vessel. The pre-manipulated length of target section is indicated at C in FIG. 8A. The optional grip texture 43 of left-side and right-side faces 42A and 42B may assist in extending the vessel. It can be seen that the closing action of working end 16 causes projecting portion 35 to move or extend target vessel section 105 into gap 33 as arms 32a and 32b straddle projecting portion 35 to stretch or extend the vessel. FIG. 8D illustrates that the targeted vessel section is extended or lengthened to a length indicated at C' from the initial length indicated at C (FIG. 8A).

This aspect of stretching or tensioning the vessel prior to RF delivery alters the impedance characteristics of the target tissue, thus enhancing RF energy delivery. Specifically, extension of the target vessel portion in FIG. 8D lowers the extracellular fluid (ECF) content of the vessel walls that are extended, thereby increasing the impedance (or resistance) of the tissue to RF current flow. Additionally, such stretching or tensioning may configured to provide a substantially uniform thickness of the target vessel, thereby ensuring a relatively uniform impedance over the length of the elongated, collapsed section of vessel.

Without limiting the method of the present invention to any particular theory, it is believed that the tissue extension or manipulation has the effect of (1) decreasing the ECF content level of the target vessel section 105 when calculated in terms of $ECF/cm^2$ of tissue mass, and (2) making the ECF level more evenly distributed throughout the targeted tissue (at the lower $ECF/cm^2$ level) whereas in the prior state, the ECF level could vary randomly within the cellular structure.

Figure 9:
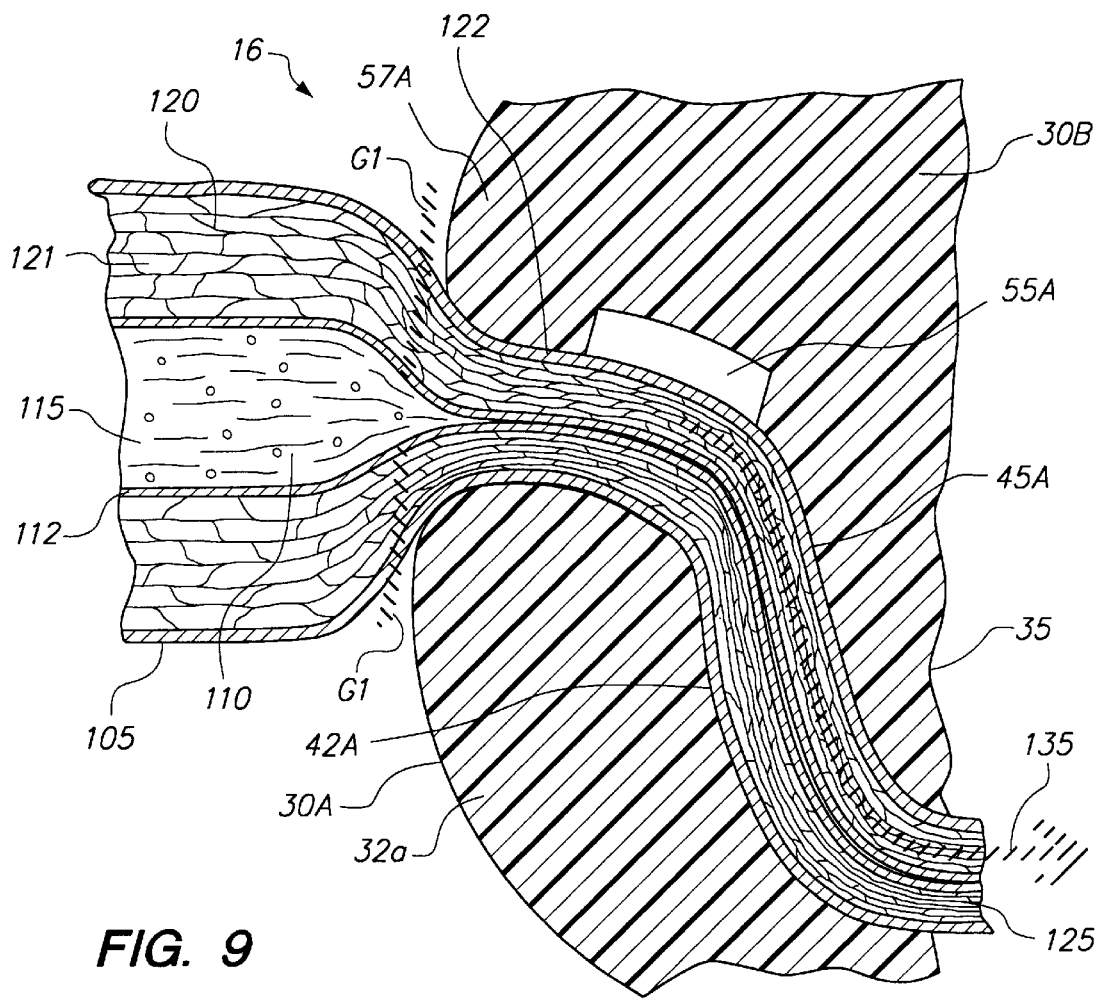
FIG. 9 is a sectional view of the targeted vessel section taken along line 9—9 of FIG. 8D.

In FIG. 9, ECF in the non-extended tissue (indicated at 120) between cells 121 is altered to a different state in the extended tissue (indicated at 122), as the extracellular fluid is squeezed out of the tissue (this is indicted graphically by the varied patterns of cell density in FIG. 9, compare locations 120 and 122). In other words, a hydration gradient G1 is created between the tissue to be treated and the tissue outside the treatment area. In this way, the RF current generally flows through the extracellular matrix to a much greater extent than passing through the intracellular fluids and cellular membranes. Arrow 135 in FIG. 9 shows the RF flow from electrode 55A toward electrode 55B (not shown).

The effects of the tissue manipulation caused by the extension of targeted vessel section 105 alternatively may be described as causing a "fuse" or "fuse point" to form in the tissue when subjected to the flow of RF current. A number of advantages are offered by creating a fuse-type effect in the targeted tissue.

First, the delivery of RF current between electrodes 55A and 55B will deliver greater levels of thermal effects for a given current flow or intensity. Thus, the targeted tissue may be elevated to a particular desired temperature to denature proteins of endothelium 112 at lower levels of RF energy delivery. It is desirable to use lower levels, rather than higher levels, of RF current intensity which, it is believed, will reduce tissue charring, smoke and odor.

Second, the requisite temperature range for tissue fusion can be reached more quickly, thus speeding up the process of tissue welding. These first two advantages provide for an enhanced energy delivery profile (delivery of current intensity over several seconds).

Figure 1B:
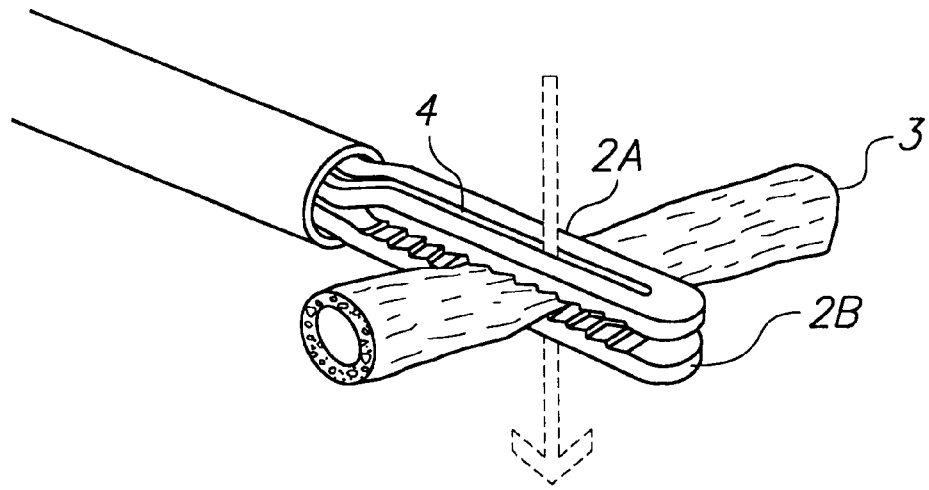

Third, the bi-polar flow longitudinally through the vessel between electrodes 55A to 55B naturally welds a longer length of vessel lumen, thereby creating a longer and more effective seal. This effect is not possible with typical prior art bi-polar devices that send current through pinched tissue between opposing jaw-electrodes (see FIG. 1B).

Fourth, it is believed that the uniformity in the ECF level in the target tissue allows for more uniform heating to provide a more uniform weld between the vessel walls.

Fifth, the bi-polar current flow longitudinally through the vessel provides little or no thermal spread outwardly along the vessel, since the current substantially flows between the paired electrodes and not outwardly. Further, the higher ECF level indicated at 120 in the vessel outwardly end portions 111A and 111B acts as a heat sink, thus preventing significant outward thermal spread. As can be seen in FIG. 9, working end 16 creates a hydration gradient G1 in the tissue where extracellular fluid is squeezed out of the tissue (cf. locations 120 and 122).

Returning to FIG. 8D, vessel section 105 is shown prepared for RF energy delivery to seal the lumen. To weld or seal the target vessel section, the surgeon actuates foot pedal 68, or another type of switch, to allow a bi-polar current to flow between electrodes 55A and 55B and longitudinally through the extended length C' of the vessel. In FIG. 9, elongate weld 125 is created where the proteins (including collagen) are denatured, intermix, and then fuse together upon cooling to fuse the vessel walls together. In delivering the flow of RF current between electrodes 55A and 55B, the surgeon may select from a number of pre-set current intensity levels to energize the targeted vessel, for example, for a time interval ranging from about 2.0 seconds to about 60.0 seconds or more, depending on current intensity level.

Preferably, a power level ranging from 1 watt to about 40 watts is applied, which is sufficient to seal the blood vessel. More preferably, the power level ranges from 2 watts to 15 watts, and still more preferably 2 watts to 10 watts, when applied to an extended (stretched) blood vessel in the bi-polar manner described herein above. The duration of RF energy delivery is determined by the surgeon's experience, by a pre-set, or by observation of the blood vessel as it is welded.

Figure 10:
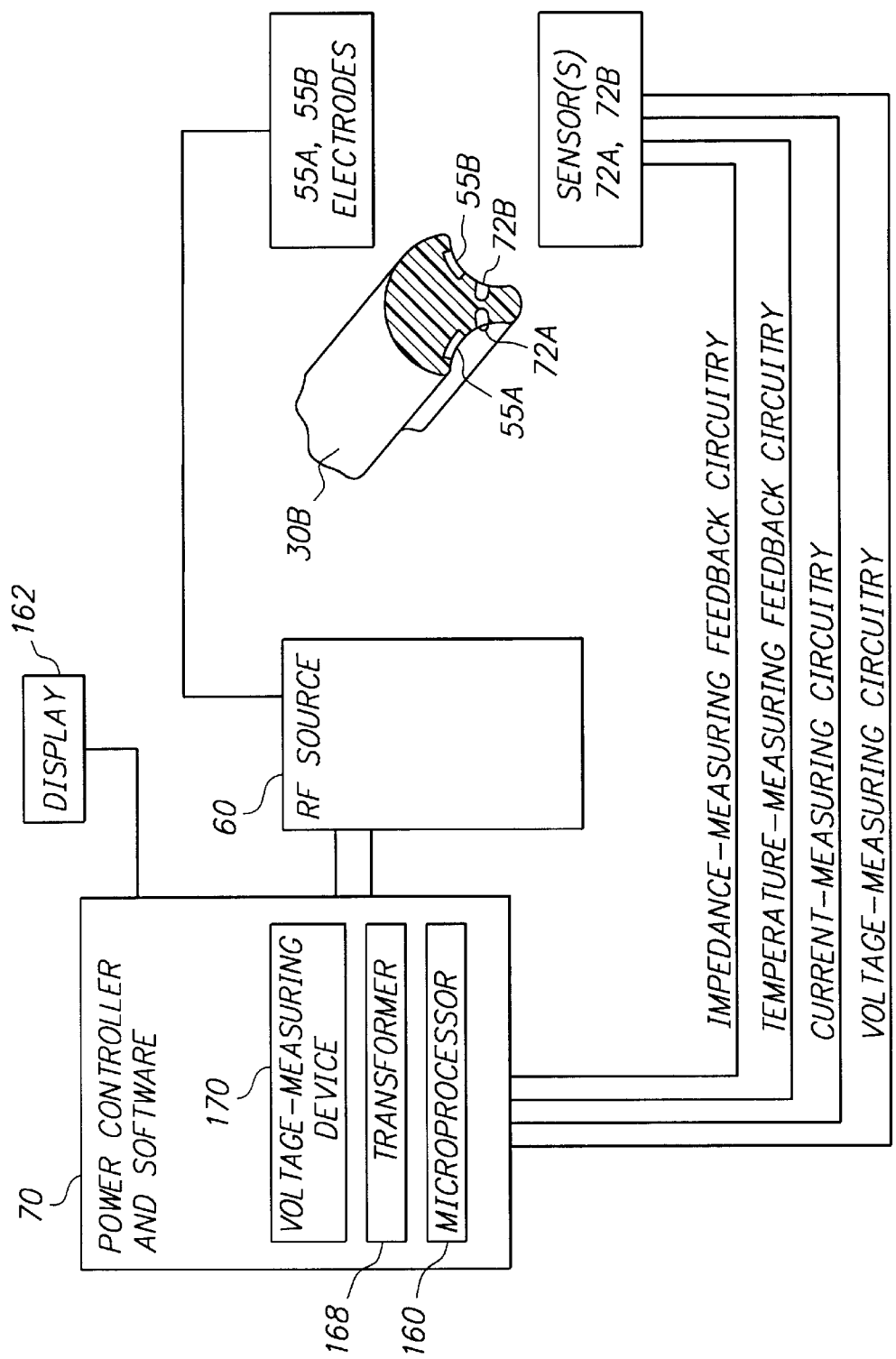
FIG. 10 is a schematic diagram of a power controller of an alternative embodiment of the apparatus of the present invention.

Referring now to FIG. 10, an alternative embodiment of the present invention is described that includes sensors 72A–72B carried by the working end 16 (as shown in FIG. 5) in combination with electronic power controller 70 indicated in FIG. 2. Sensors 72A–72B are adapted to send feedback signals to power controller 70, which modulates the delivery of RF energy delivery to the instrument. Power controller 70 is shown in FIG. 2 interconnecting RF source 60 and instrument 5.

Power controller 70 controls delivery of RF power in a bi-polar manner between paired electrodes 55A and 55B, according to predetermined parameters. Power controller 70 may be designed to selectively control power delivery to the electrodes in varied operational modes. The power controller 70, which typically includes microprocessor 160 together with appropriate software, may be programmed to deliver power according to preset parameters. On the power controller 70, there may be a keyboard, disk drive or other non-volatile memory system, and displays as are well known in the art for operating the system. Operator interface 162 may include various types of imaging systems for observing the RF treatment cycle such as thermal sensor displays and/or impedance monitoring displays.

In a preferred manner of operation of instrument 5 for vessel welding, or impedance-controlled operational mode, power controller 70 is programmed to receive signals and values for tissue impedance within the target tissue section 105 (see FIG. 8D) during operation. For example, programmed values typically may include a maximum impedance or resistance level (estimated or known) for the tissue portion targeted for welding and a minimum impedance or resistance level (also known or estimated).

Power controller 70 preferably includes impedance measuring circuitry adapted to measure impedance levels and feedback circuitry that controls power delivery responsive to the measured levels. The impedance measuring circuitry converts current and voltage signals into an actual impedance level and signal responsive to RF current flow between paired bi-polar electrodes 55A and 55B and the RF voltage connected across the paths between the electrodes. Current measuring device 168 (e.g., a transformer) and a voltage measuring device 170 are operatively connected to RF source 60 and the electrode pair.

Power controller 70 responds to signals generated by the impedance measuring circuitry to control RF energy delivered to the electrodes. Typically, the controller selects a particular impedance or resistance level between the maximum and minimum impedance levels and turns off or modulates RF power delivery to the electrodes when either (i) actual measured impedance reaches the particular level, or (ii) the rate (over time) of the rise in actual impedance toward the particular selected level exceed a parameter as it rises toward the maximum impedance level. For example, the particular impedance level, or particular rate of change, may relate a particular level just below the maximum level or an average level between the selected maximum and minimum impedance levels.

In an alternative mode of operation, referred to as a temperature-controlled operational mode, the operator selects a target temperature level, typically a known temperature at which proteins will weld the targeted vessel. Temperature signals measured by a sensor or sensor array 72A and 72B are continuously provided to control the level of power delivery to the electrodes. The power controller thus can measure the difference between the actual temperature measured (or averaged) by sensors 72A and 72B and a target temperature level and thereafter select a power delivery level or delivery profile proportional to the temperature difference at any point in time during an energy delivery cycle.

The power controller further may be programmed to control power delivery based on temperature signals such that, if a particular temperature is exceeded at either sensor location, power delivery is terminated. The operator also may set a target temperature level which is to be maintained at a particular sensor site or averaged among several sensor sites. Additionally, a timing device may be included, thereby enabling the operator to maintain a particular temperature at any sensor site (or combination thereof) for a particular length of time. Accordingly, a power delivery profile may be programmed into controller 70 to deliver RF energy over a period of time to achieve a target temperature level. Alternatively, the power controller may accept a presset time for reaching a particular temperature level.

In yet another aspect of the present invention, the controller may operate in a combined temperature/impedance-controlled operational mode, having the combined features described hereinabove, to still more precisely control or modulate RF power delivery. In addition, all of these modes of operation may be combined to provide a desired temperature (or average temperature) at one or more sensor locations in the jaw assembly such that energy delivery terminates if a maximum pre-set temperature is reached. Impedance control may be employed, as previously described, to modulate or control power delivery based on impedance levels to achieve a particular sensed temperature or temperature profile. Thus, the temperature at the sensor array can be maintained at a pre-set temperature based on impedance feedback unless a maximum temperature is exceeded, at which energy delivery is modulated or terminated.

Power controller 70 also may include circuitry for measuring actual power output delivery based on the actual power output signal. In this mode of operation, referred to as a power-controlled operational mode, the operator selects a target actual power delivery for treating tissue, which is typically a level of actual energy deposition, in joules, known or estimated to achieve a certain temperature in the target tissue. A time profile then may be programmed into controller 70 to deliver an actual amount of power over a particular period of time to achieve a target energy delivery (and temperature) in tissue. Thus, the power controller delivers RF energy at or along a continuous range of pre-set power levels or according to a pre-set power delivery profile (RF power delivery over a period of time), which pre-sets may be indicated by a power level delivery signal or power profile signal.

Thus, the power controller and software of the present invention, together with the above described feedback circuitry, are capable of full process monitoring and continuous control of following operational variables: (i) power delivery; (ii) time, temperature and impedance parameters of a selected energy delivery cycle, and; (iii) vectoring RF current delivery in different directions between the electrodes. Additionally, power controller 70 besides vectoring RF current between the electrodes monitors circuit continuity for each electrode.

Microprocessor 160 may be programmed to sequentially receive and store digital data representing impedance and temperature values. Those values also may be displayed on operator interface as numerical values. The temperature and impedance values are compared by microprocessor 160 with pre-programmed temperature and impedance limits, as described above. When the measured temperature value or impedance value at a particular site exceeds a predetermined limit, a warning or other indication is given on the operator interface (such a warning light); at the same time the delivery of energy to a particular electrode site is decreased or terminated. Calculated surface temperatures of the vessel may be forwarded by controller 70 to the display and compared to a predetermined limit to activate a warning indicator on the display.

As will be appreciated, the preferred embodiments described hereinabove are especially adapted to weld blood vessels. The principles of the present invention may be readily adapted to similar device (not shown) that further includes a reciprocating blade member, such as are known in the art, for transecting the welded vessel with a slot in gap 33 of the proximal jaw side 30A. Such a reciprocating blade could be actuated by any suitable means from handle 7. Alternatively, a separate rotatable scissors-type blade (not shown) may be provided for transecting the welded blood vessel.

The present invention may be readily adapted for use in sealing other organs or anatomic structures having a lumen surrounded by walls containing proteins, for example collagen, that may be denatured and intermixed to form a thermal biological glue. It is believed that most tubular organs in the body have walls that are capable of such RF welding utilizing the techniques disclosed herein. For example, various lumens in a patient's body may be sealed such intestines, ducts, intestinal defects such as diverticulitis, and any other tubular organs or conduits in a patient's body.

Although particular embodiments of the present invention have been described above in detail, it will be understood that this description is merely for purposes of illustration. Specific features of the invention are shown in some drawings and not in others, and this is for convenience only and any feature may be combined with another in accordance with the invention. Further variations will be apparent to one skilled in the art in light of this disclosure and are intended to fall within the scope of the appended claims.

What is claimed is:

1. Apparatus for welding a vessel comprising:
   a first member having a first vessel engaging surface;
   a second member having a second vessel engaging surface and right and left lateral portions, the second vessel engaging surface disposed in opposing relation to the first vessel engaging surface, the second member operatively coupled to the first member to grasp the vessel to define an engagement plane, the right and left lateral portions deflecting outwardly away from one another to elongate the engagement plane when the first member engages the second member; and
   first and second bi-polar electrodes disposed in spaced apart relation on one of the first and second members and adapted to be in communication with the engagement plane, the first and second bi-polar electrodes adapted to be coupled to a source of RF energy to provide a flow of current between the first and second bi-polar electrodes.

2. The apparatus of claim 1 wherein the engagement plane defines a curvilinear surface.

3. The apparatus of claim 1 wherein the first member forms a mating surface to the second member.

4. The apparatus of claim 3 wherein the first and second members comprise first and second opposing jaw members, respectively.

5. The apparatus of claim 4 further comprising an actuation mechanism for moving at least one of the first and second opposing jaw members towards and away from the other.

6. The apparatus of claim 5 wherein the right and left lateral portions define a gap therebetween, the second jaw member further comprising means for biasing the right and left lateral portions inwards towards one another.

7. The apparatus of claim 6 wherein the first jaw member further comprises an elongated portion that extends within the gap when the first and second jaw members close together, the means for biasing retaining the right and left lateral portions of the second jaw member in contact with the elongated portion of first jaw member when the first jaw member contacts the second jaw member.

8. The apparatus of claim 1 wherein the first and second bi-polar electrodes are disposed on the first member.

9. The apparatus of claim 1 further comprising a sensor disposed on one of the first and second members.

10. The apparatus of claim 9 wherein the sensor is a temperature sensor, the apparatus further comprising an RF power controller that modulates the RF energy responsive to an output of the temperature sensor.

11. A method for welding a vessel comprising:
providing an instrument comprising a first member having a first vessel engaging surface and a second member having a second vessel engaging surface and right and left lateral portions, the second vessel engaging surface disposed in opposing relation to the first vessel engaging surface;
identifying a vessel to be sealed, the vessel having first and second ends;
engaging the vessel at the first and second ends between the first and second members;
contacting an intermediate portion of the vessel at a location between the first and second ends;
longitudinally extending the intermediate portion of the vessel located between the first and second ends by deflecting the right and left lateral portions outwardly away from one another to elongate the engagement plane;
contacting first and second bi-polar electrodes to the vessel in spaced apart relation; and
applying an RF current between the first and second electrodes so that the RF current flows through and welds the intermediate portion of the vessel.

12. The method of claim 11 further comprising, prior to contacting the first and second bi-polar electrodes to the vessel in spaced apart relation, collapsing the intermediate portion of the vessel to approximate opposing vessel walls.

13. The method of claim 11 wherein longitudinally extending the intermediate portion of the vessel further comprises altering an impedance of the intermediate portion.

14. The method of claim 13 wherein longitudinally extending the intermediate portion of the vessel further comprises reducing an extracellular fluid content of the vessel.

15. The method of claim 13 wherein longitudinally extending the intermediate portion of the vessel further comprises reducing the intermediate portion to a substantially uniform thickness.

16. The method of claim 13 wherein longitudinally extending the intermediate portion of the vessel to alter an impedance of the intermediate portion further comprises making the impedance of the intermediate portion substantially uniform.

17. The method of claim 11 further comprising contacting a sensor to the intermediate portion of the vessel.

18. The method of claim 17 wherein the sensor monitors temperature of the intermediate portion of the vessel and generates an output signal, the method further comprising modulating the RF current applied to the intermediate portion responsive to the output signal.

19. The method of claim 18 wherein the sensor monitors impedance of the intermediate portion of the vessel and generates an output signal, the method further comprising modulating the RF current applied to the intermediate portion responsive to the output signal.

20. The method of claim 11 further comprising:
monitoring energy delivered to the intermediate portion of the vessel;
generating an output signal corresponding to the energy delivered to the intermediate portion of the vessel; and
modulating the RF current applied to the intermediate portion responsive to the output signal.

* * * * *